United States Patent
Zhu

(10) Patent No.: US 9,623,232 B2
(45) Date of Patent: Apr. 18, 2017

(54) METHOD AND APPARATUS FOR IDENTIFYING MIDDLE LEAD IN A TRI-LEAD CONFIGURATION

(75) Inventor: Changfang Zhu, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 2095 days.

(21) Appl. No.: 12/606,024

(22) Filed: Oct. 26, 2009

(65) Prior Publication Data
US 2010/0137943 A1 Jun. 3, 2010

Related U.S. Application Data

(60) Provisional application No. 61/119,653, filed on Dec. 3, 2008.

(51) Int. Cl.
  *A61N 1/05* (2006.01)
  *A61N 1/36* (2006.01)
  *A61N 1/08* (2006.01)

(52) U.S. Cl.
  CPC ......... *A61N 1/0531* (2013.01); *A61N 1/0534* (2013.01); *A61N 1/0551* (2013.01); *A61N 1/36071* (2013.01); *A61N 1/0553* (2013.01); *A61N 1/08* (2013.01)

(58) Field of Classification Search
  CPC .. A61N 1/0531; A61N 1/0534; A61N 1/0551; A61N 1/0553; A61N 1/36; A61N 1/36071
  USPC .......... 607/9, 28, 115, 116, 128, 2; 128/898
  See application file for complete search history.

(56) References Cited

U.S. PATENT DOCUMENTS

| | | | |
|---|---|---|---|
| 4,435,681 A * | 3/1984 | Masuda | G01N 27/62 324/459 |
| 5,895,416 A * | 4/1999 | Barreras et al. | 607/62 |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,317,948 B1 | 1/2008 | King et al. | |
| 2006/0122654 A1* | 6/2006 | Bradley et al. | 607/28 |
| 2007/0150036 A1 | 6/2007 | Anderson | |
| 2007/0168004 A1 | 7/2007 | Walter | |

(Continued)

OTHER PUBLICATIONS

J.J. Struijk et al., Transverse Tripolar Spinal Cord Stimulation: Theoretical Performace of a Dual Channel System, Med. & Biol. Eng. & Comput., 1996, 34, 273-279.

(Continued)

*Primary Examiner* — Christopher A Flory
(74) *Attorney, Agent, or Firm* — Schwegman Lundberg & Woessner, P.A.

(57) ABSTRACT

A method and medical system for operating three electrodes electrically coupled to three proximal contacts carried by three lead bodies is provided. The electrodes are implanted adjacent tissue of a patient and include a middle electrode and a pair of electrodes flanking the middle electrode. Electrical energy is conveyed between three different pairs of the proximal contacts, thereby respectively generating three electrical fields in the tissue between three electrode pairs. A potential of each of the electrical fields is measured at the remaining electrodes via the remaining proximal contacts, respectively. The lead body associated with the middle electrode is identified based on the measured electrical field potentials.

8 Claims, 12 Drawing Sheets

(56) References Cited

U.S. PATENT DOCUMENTS

| | | | | |
|---|---|---|---|---|
| 2008/0004674 A1* | 1/2008 | King | ............. | A61N 1/0529 |
| | | | | 607/46 |
| 2008/0004675 A1* | 1/2008 | King | ............. | A61N 1/0529 |
| | | | | 607/59 |
| 2008/0046036 A1* | 2/2008 | King | ............. | A61N 1/0529 |
| | | | | 607/59 |
| 2009/0157136 A1* | 6/2009 | Yang | ............. | A61B 5/0422 |
| | | | | 607/17 |
| 2009/0216306 A1 | 8/2009 | Barker | | |

OTHER PUBLICATIONS

J. Holsheimer, Ph.D., et al., Clinical Evaluation of Paresthesia Steering with a New System for Spinal Cord Stimulation, Neurosurgery, vol. 42, No. 3, Mar. 1998, 541-549.
U.S. Appl. No. 61/030,506, Temporary Neurostimulation Lead Identification Device, Inventor: John M. Barker, filed Feb. 21, 2008.
U.S. Appl. No. 11/557,484, System and Method for Computationally Determining Migration of Neurostimulation Leads, Inventor: Michael M .Moffit, filed Nov. 7, 2006.

* cited by examiner

FIG. 11(a)

| Electrode Separation | Lead Body Orientation | Ideal case | | | Error tolerance | | | Error tolerance | | |
|---|---|---|---|---|---|---|---|---|---|---|
| | | M1 | M2 | M3 | M1 | M2 | M3 | M1 | M2 | M3 |
| $r_{lm} \sim r_{mr} < r_{lr}$ | L2 / L1 / L3 | ~0 | − | + | − | − | High+ | + | − | High+ |
| $r_{lm} \sim r_{mr} < r_{lr}$ | L3 / L1 / L2 | ~0 | − | + | + | High− | + | − | High− | + |
| $r_{lm} < r_{mr} < r_{lr}$ | L2 / L1 / L3 | − | − | High+ | − | High− | + | − | High− | + |
| $r_{lm} < r_{mr} < r_{lr}$ | L3 / L1 / L2 | + | High− | + | High+ | − | + | + | − | + |
| $r_{mr} < r_{lm} < r_{lr}$ | L2 / L1 / L3 | + | High− | + | High+ | − | + | + | − | High+ |
| $r_{mr} < r_{lm} < r_{lr}$ | L3 / L1 / L2 | − | − | High+ | High− | − | + | − | High− | + |

Lead 1 in the middle

METHOD AND APPARATUS FOR IDENTIFYING MIDDLE LEAD IN A TRI-LEAD CONFIGURATION

RELATED APPLICATION

The present application claims the benefit under 35 U.S.C. §119 to U.S. provisional patent application Ser. No. 61/119,653, filed Dec. 3, 2008. The foregoing application is hereby incorporated by reference into the present application in its entirety.

FIELD OF THE INVENTION

The present invention relates to tissue stimulation systems, and more particularly, to apparatus and methods for identifying neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more stimulation leads implanted at the desired stimulation site and an implantable neurostimulator, such as an implantable pulse generator (IPG), implanted remotely from the stimulation site, but coupled either directly to the stimulation leads or indirectly to the stimulation leads via one or more lead extensions in cases where the length of the stimulation leads is insufficient to reach the IPG. Thus, electrical pulses can be delivered from the neurostimulator to the stimulation leads to stimulate the tissue and provide the desired efficacious therapy to the patient.

In the context of an SCS procedure, one or more stimulation leads are introduced through the patient's back into the epidural space under fluoroscopy, such that the electrodes carried by the leads are arranged in a desired pattern and spacing to create an electrode array. The specific procedure used to implant the stimulation leads will ultimately depend on the type of stimulation leads used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the special cord. A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

After proper placement of the stimulation leads at the target area of the spinal cord, the leads are anchored in place at an exit site to prevent movement of the stimulation leads. To facilitate the location of the neurostimulator away from the exit point of the stimulation leads, lead extensions are sometimes used. Whether lead extensions are used or not, the proximal ends of the stimulation leads exiting the spinal column are passed through a tunnel subcutaneously formed along the torso of the patient to a subcutaneous pocket (typically made in the patient's abdominal or buttock area) where a neurostimulator is implanted. The subcutaneous tunnel can be formed using a tunneling tool over which a tunneling straw may be threaded. The tunneling tool can be removed, the stimulation leads threaded through the tunneling straw, and then the tunneling straw removed from the tunnel while maintaining the stimulation leads in place within the tunnel.

The stimulation leads are then connected directly to the neurostimulator by inserting the proximal ends of the stimulation leads within one or more connector ports of the IPG or connected to lead extensions, which are then inserted into the connector ports of the IPG. The IPG can then be operated to generate electrical pulses that are delivered, through the electrodes, to the targeted tissue, and in particular, the dorsal column and dorsal root fibers within the spinal cord.

The stimulation creates the sensation known as paresthesia, which can be characterized as an alternative sensation that replaces the pain signals sensed by the patient. Intraoperatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computerized programming system, such as Bionic Navigator®, available from Boston Scientific Neuromodulation Corporation, can be used to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

To produce the feeling of paresthesia without inducing discomfort or involuntary motor movements within the patient, it is often desirable to preferentially stimulate nerve fibers in the dorsal column (DC) nerve fibers, which primarily include sensory nerve fibers, over nerve fibers in the dorsal root (DR) nerve fibers, which include both sensory nerve fibers and motor reflex nerve fibers. In order to stimulate the DC nerve fibers, while guarding against the stimulation of the DR nerve fibers, tripolar SCS systems may activate anodes that flank a single cathode in a medial-lateral electrical field, with the single cathode providing the stimulation energy for the DC fibers, while the flanking anodes guarding against the over-stimulation of the DR fibers, thereby increasing the therapeutic range of SCS for stimulating the desired DC fibers, while reducing the unwanted side effect of stimulating DR fibers (see J. J. Struijk and J. Holsheimer Tripolar Spinal Cord Stimulation: Theoretical Performance of a Dual Channel System, Medical and Biological Engineering and Computing, Vol. 34, No. 4, 1996, pp. 273-279; J. Holsheimer, B. Nuttin, G. King, W. Wesselink, J. Gybels, and P. de Sutter, Clinical Evaluation of Paresthesia Steering with a New System for Spinal Cord Stimulation, Neurosurgery, Vol. 42, No. 3, 1998, pp. 541-549).

When programming a transverse tripolar system, knowing which electrode is in the middle of the medio-lateral electrode arrangement is absolutely critical to selecting the cathode that provides the stimulation, as well as selecting the anodes that provide the guarding function. Once the lead or leads have been implanted, identifying the middle electrode column or middle stimulation lead can be challenging, especially in those tripolar systems constructed of individual leads. Additionally, in the case where multiple percutaneous leads are used to construct the medio-lateral electrode arrangement, knowing the relative proximity of the lateral leads to the middle lead is also helpful in sculpting the current applied to each guarding anode.

Oftentimes, multiple lead bodies may extend from the spinal region of the patient. For example, multiple percutaneous leads may be implanted within the patient adjacent the spinal cord, or in the case of paddle leads, multiple lead tails may extend from the paddle, with each lead tail being coupled to specific electrodes on the paddle. Because the programming of the IPG will depend upon the physical locations of the electrodes relative to the patient's spinal cord (especially in the case of a tripolar system as just described), the proximal ends of the lead bodies may be labeled before passing them through the tunneling straw, so that the surgeon can keep track of which set of electrodes is connected to which connector port on the implanted IPG (which may include three ports for a medio-lateral electrode arrangement).

One technique used by surgeons to identify the lead bodies is to tie sutures around the proximal ends of the lead bodies prior to introducing them through the tunneling straw; for example, one suture around a first lead body, two sutures around a second lead body, three sutures around a third lead body, etc. Once the proximal ends of the lead bodies exit the tunneling straw, the surgeon can then identify each lead body (and thus the corresponding electrodes) by the number of sutures tied to the respective lead body, thereby allowing the lead body to be connected to the correct port on the IPG.

While this technique can be successfully employed to identify lead bodies, it considerably extends the length of the surgery time, which is undesirable. In some cases, the identification features, such as different colors or markings, can be incorporated into the proximal ends of the lead bodies, such that the lead bodies can be identified as they exit the tunneling straw. Also, it is possible that the distal ends of the lead bodies may have been mixed up during lead insertion, and therefore, the visual identifiers will not correspond to their intended electrodes. Even with the use of visual identifiers, however, the proximal ends of the lead bodies can still be inserted into the incorrect connector ports, or the distal ends of the lead bodies may have been mixed up during lead insertion, and therefore, the visual identifiers will not correspond to their intended electrodes. If the lead bodies are inserted into the incorrect connector ports, intra-operative testing of the lead placement may be compromised. Additional surgical time may be wasted to identify and correct the connection problem. If the errors remain unidentified, the patient may leave the operating room with the lead bodies incorrectly connected. During post-operative fitting, additional time may then be lost identifying and compensating for lead bodies that are not in the proper connector ports. This ultimately can result in sub-optimal therapy.

Another technique that can be used to identify the lead bodies is to individually activate stimulation for each electrode column and request the patient to provide paresthesia feedback (e.g., feeling from left, right, or both sides of the body) in order to determine the medio-lateral order of the electrode columns. This could be time-consuming and may become confusing if the middle lead is placed laterally to the spinal cord physiological midline. Also, this conventional method may not be able to reveal the relative proximity of the two lateral leads absent a fluoroscopic procedure.

There, thus, remains a need for a quick, effective, and low-cost method for identifying a lead body of a neurostimulation lead corresponding to a specific electrode in an arrangement of three electrodes (e.g., medio-lateral electrode arrangement), as well as to determine the relative distances between the three electrodes.

SUMMARY OF THE INVENTION

In accordance with a first aspect of the present inventions, a method of operating three electrodes electrically coupled to three proximal contacts carried by three lead bodies, respectively, is provided. The lead bodies can, e.g., form a portion of a surgical paddle lead or may respectively form portions of three percutaneous leads. The electrodes are located adjacent tissue of a patient (e.g., spinal cord tissue) and include a middle electrode and a pair of electrodes flanking the middle electrode. The method comprises conveying electrical energy between at least one pair of the proximal contacts, thereby generating at least one electrical field in the tissue between at least one pair of the electrodes, respectively. The method further comprises measuring a potential of at least one electrical field generated between the electrode pair(s) at least one remaining electrode via the remaining proximal contact(s), respectively. The method further comprises identifying the lead body associated with the middle electrode based on the measured electrical field potential(s).

In one method, the proximal contact pair(s) comprises three pairs of proximal contacts, the electrode pair(s) comprises three pairs of electrodes, the electrical field(s) comprises three electrical fields, and the measured electrical field potential(s) comprise three measured electrical field potentials. In this case, the lead body associated with the middle electrode may be identified at least partially based on a polarity of at least one of the three measured electrical field potentials, and/or at least partially based on an amplitude value of at least one of the three measured electrical field potentials, and/or at least partially based on the highest amplitude value between the three measured electrical field potentials. If one of the flanking electrodes is a greater distance from the middle electrode than the other flanking electrode, the method may further comprise identifying the lead body associated with the flanking electrode that is further from the middle electrode based on the three measured electrical field potentials.

In another method, the three electrodes are respectively located within three electrode columns. In this case, the method may further comprise determining a longitudinal stagger between the three electrode columns, and selecting the three electrodes from the respective electrode columns based on the determined longitudinal stagger. Preferably, if there is a longitudinal stagger, the electrodes can be selected from the respective electrode columns to have the least amount of longitudinal stagger.

In still another method, the identification of the lead body comprises comparing the measured electrical field potential(s) to each of a plurality of reference electrical field potential sets respectively corresponding to different lead body orientations, determining a match between the at least one measured electrical field potential and one of the reference electrical field potential sets, and identifying the lead body associated with the middle electrode from the matching reference electrical field potential set. The method may further comprise programming a neurostimulator with a plurality of stimulation parameters based on the identified lead body.

In accordance with a second aspect of the present inventions, a medical system is provided. The system comprises one or more neurostimulation leads (e.g., a single surgical paddle lead or three percutaneous leads) comprising three electrodes and three lead bodies carrying three proximal contacts electrically coupled to the three electrodes, respectively. The electrodes are configured for being placed adjacent tissue as a middle electrode and a pair of electrodes flanking the middle electrode. The system further comprises a controller configured for transmitting electrical energy conveying electrical energy between at least one pair of the proximal contacts, thereby generating at least one electrical field in the tissue between at least one pair of the electrodes, respectively. The medical system further comprises monitoring circuitry configured for measuring a potential of the electrical field(s) at least one remaining electrode via at least one remaining proximal contact, respectively. The medical system further comprises the at least one processor configured for identifying the lead body associated with the middle electrode based on the measured electrical field potential(s).

In one embodiment, the proximal contact pair(s) comprises three pairs of proximal contacts, the electrode pair(s) comprises three pairs of electrodes, the electrical field(s) comprises three electrical fields, and the measured electrical field potential(s) comprise three measured electrical field potentials. In this case, the processor(s) may be configured for identifying the lead body associated with the middle electrode at least partially based on a polarity of at least one of the three measured electrical field potentials, and/or at least partially based on an amplitude value of at least one of the three measured electrical field potentials, and/or at least partially based on the highest amplitude value between the three measured electrical field potentials. If one of the flanking electrodes is a greater distance from the middle electrode than the other flanking electrode, the processor(s) may be configured for identifying the lead body associated with the flanking electrode furthest from the middle electrode based on the three measured electrical field potentials.

In another embodiment, the three electrodes are respectively located within three electrode columns. In this case, the processor(s) may be further configured for determining a longitudinal stagger between the three electrode columns, and selecting the three electrodes from the respective electrode columns based on the determined longitudinal stagger. Preferably, if there is a longitudinal stagger, the processor(s) can be configured for selecting the electrodes from the respective electrode columns to have the least amount of longitudinal stagger.

In still another embodiment, the identification of the lead body comprises comparing the measured electrical field potential(s) to each of a plurality of reference electrical field potential sets respectively corresponding to different lead body orientations, determining a match between the at least one measured electrical field potential and one of the reference electrical field potential sets, and identifying the lead body associated with the middle electrode from the matching reference electrical field potential set.

In yet another embodiment, the system further comprises memory storing a plurality of reference electrical field potential sets respectively corresponding to different lead body orientations. In this case, the processor(s) is configured for identifying the lead body by comparing the measured electrical field potential(s) to each of the reference electrical field potential sets, determining a match between the measured electrical field potential(s) and one of the reference electrical field potential sets, and identifying the lead body associated with the middle electrode from the matching reference electrical field potential set. The system may, e.g., comprise a neurostimulator containing the controller, and an external control device containing the processor(s), or alternatively, may simply comprise a neurostimulator that contains the both the controller and the processor(s). Alternatively, if there are multiple processors, one can be contained within a neurostimulator and one can be contained within an external control device.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 11a-11c are look-up tables containing reference bipolar electrical field potential measurements that can be compared to the actual bipolar electrical field potential measurements by the SCS system of FIG. 1 to determine lead body orientations relative to the electrode columns of FIG. 9;

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
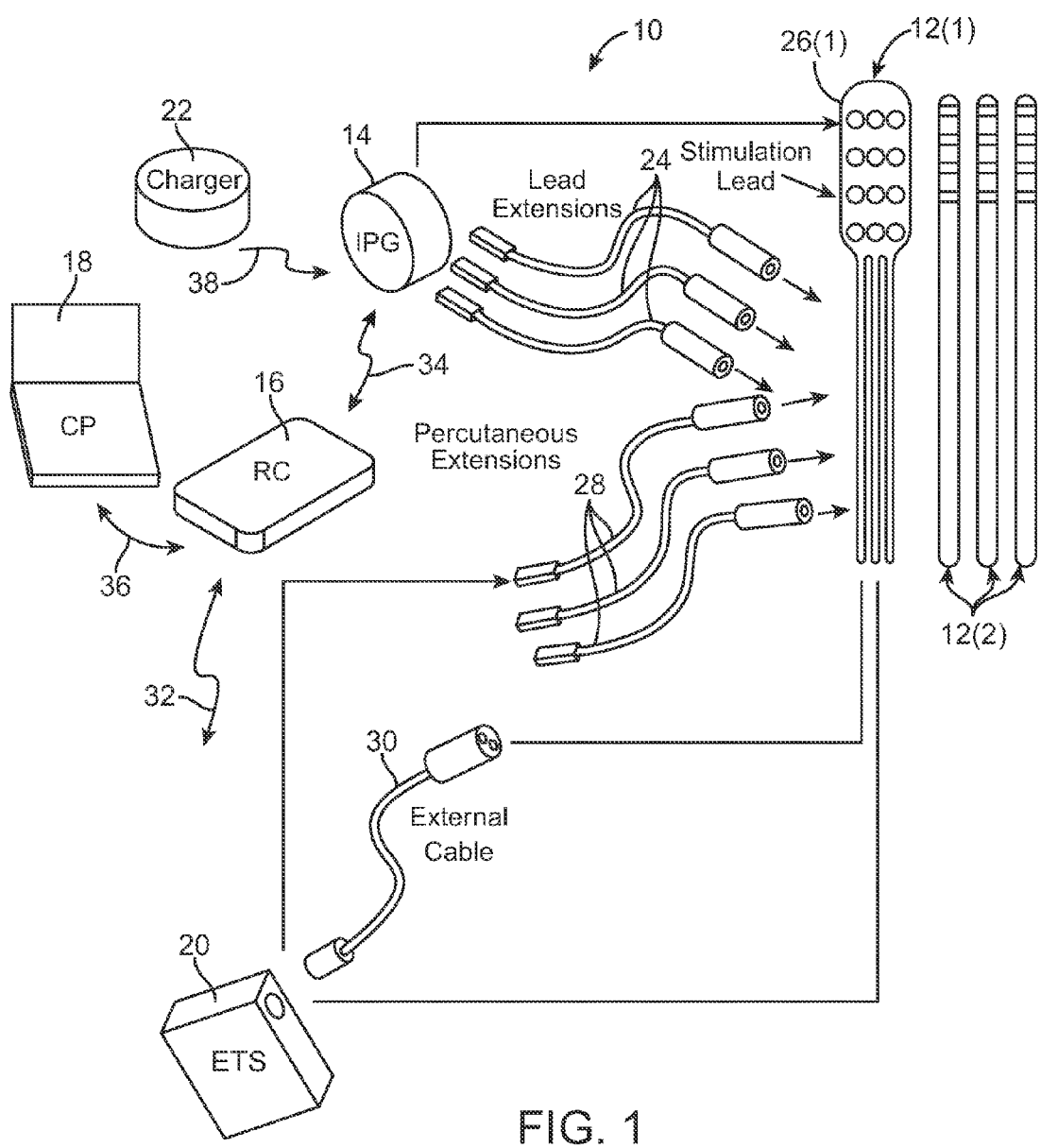
FIG. 1 is plan view of one embodiment of a spinal cord stimulation (SCS) system arranged in accordance with the present inventions.

Turning first to FIG. 1, an exemplary SCS system 10 generally comprises at least one implantable stimulation lead 12 (e.g., a surgical paddle lead 12(1) and/or multiple percutaneous leads 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via three lead extensions 24 to the stimulation lead(s) 12, which carries a plurality of electrodes 26 arranged in an array. In the illustrated embodiment, the surgical paddle lead 12(1) carries three columns of electrodes 26, and the three percutaneous leads 12(2) respectively carry three columns of electrodes 26. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the stimulation lead 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

As briefly discussed above, one of the stimulation leads may be a surgical paddle lead 12(1). To this end, and with reference to FIG. 2, the surgical paddle lead 12(1) comprises a paddle-shaped membrane 40, and three elongated lead bodies 42 extending from the paddle-shaped membrane 40. Each of the lead bodies 42 has a proximal end 44 and a distal end 46. Each lead body 42 may, e.g., have a diameter within the range of 0.03 inches to 0.07 inches and a length within the range of 30 cm to 90 cm for spinal cord stimulation applications. Each lead body 42 may be composed of a suitable electrically insulative and biocompatible material, such as, a polymer (e.g., polyurethane or silicone), and may be extruded from as a unibody construction. The paddle-shaped membrane 40 is composed of an electrically insulative and biocompatible material, such as silicone.

The surgical paddle lead 12(1) further comprises proximal contacts 48 mounted to the proximal ends 44 of the lead bodies 42 and the plurality of electrodes 26 mounted on one side of the paddle-shaped membrane 40 in a two-dimensional arrangement. In the illustrated embodiment, proximal contacts 48 are labeled as PC1-PC12, with proximal contacts PC1-PC4 being mounted to the proximal end 44 of the first lead body 42, proximal contacts PC5-PC8 being mounted to the proximal end 44 of the second lead body 42, and proximal contacts PC9-PC12 being mounted to the proximal end 44 of the third lead body 42. The electrodes 26 are arranged as a first column of electrodes labeled E1-E4, a second column of electrodes labeled E5-E8, and a third column of electrodes E9-E12. Although the stimulation lead 12(1) is shown as having twelve electrodes 26 (and thus, twelve corresponding proximal contacts 48 on the lead bodies 42), the number of electrodes may be any number suitable for the application in which the surgical paddle lead 12(1) is intended to be used (e.g., three, six, twenty-four, thirty-six, etc.).

Each of the electrodes 26 takes the form of a disk composed of an electrically conductive, non-corrosive, material, such as, e.g., platinum, titanium, stainless steel, or alloys thereof. Each of the proximal contacts 48 takes the form of a cylindrical ring element composed of an electrically conductive, biocompatible, non-corrosive, material, such as, e.g., platinum, titanium, stainless steel, or alloys thereof.

The surgical paddle lead 12(1) also includes a plurality of electrical conductors (not shown) extending through individual lumens (not shown) within each lead body 42 and connected between the respective proximal contacts 48 and electrodes 26 using suitable means, such as welding, thereby electrically coupling the proximal contacts PC1-PC4 to the distally-located electrodes E1-E4, the proximal contacts PC5-PC8 to the distally-located electrodes E5-E8, and the proximal contacts PC9-PC12 to the distally-located electrodes E9-E12.

Further details regarding the construction and method of manufacture of paddle leads are disclosed in U.S. patent application Ser. No. 11/319,291, entitled "Stimulator Leads and Methods for Lead Fabrication," the disclosure of which is expressly incorporated herein by reference.

As briefly discussed above, instead of a surgical paddle lead, three percutaneous leads 12(2) may be used. To this end, and with reference to FIG. 3, each percutaneous lead 12(2) comprises an elongated lead body 42 having a proximal end 44 and a distal end 46. Each lead body 42 may, e.g., have a diameter within the range of 0.03 inches to 0.07 inches and a length within the range of 30 cm to 90 cm for spinal cord stimulation applications. The lead body 42 may be composed of a suitable electrically insulative and biocompatible material, such as, a polymer (e.g., polyurethane or silicone), and may be extruded from as a unibody construction.

Each percutaneous lead 12(2) further comprises a plurality of proximal contacts 48 mounted to the proximal end 44 of the lead body 42 and the plurality of in-line electrodes 26 mounted to the distal end 46 of the lead body 42. As shown, the electrodes 26 are labeled E1-E12, and the proximal contacts 48 are labeled as PC1-PC12. Although each of the percutaneous leads 12(2) is shown as having four electrodes 26 (and thus, four corresponding proximal contacts 48), the number of electrodes may be any number suitable for the application in which the percutaneous lead 12(2) is intended to be used (e.g., one, two, eight, sixteen, etc.). Each of the electrodes 26 and proximal contacts 48 takes the form of a cylindrical ring element composed of an electrically conductive, biocompatible, non-corrosive, material, such as, e.g., platinum, titanium, stainless steel, or alloys thereof, which is circumferentially disposed about the lead bodies.

Each percutaneous lead 12(2) also includes a plurality of electrical conductors (not shown) extending within the lead body 42 and connected between the respective proximal contacts 48 and electrodes 26 using suitable means, such as welding, thereby electrically coupling the proximal contacts PC1-PC4 with the distally-located electrodes E1-E4, the proximal contacts PC5-PC8 with the distally-located electrodes E5-E8, and the proximal contacts PC9-PC12 with the distally-located electrodes E9-E12. Each percutaneous lead 12(2) further includes a central lumen (not shown) that may be used to accept an insertion stylet (described in further detail below) to facilitate lead implantation.

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 2:
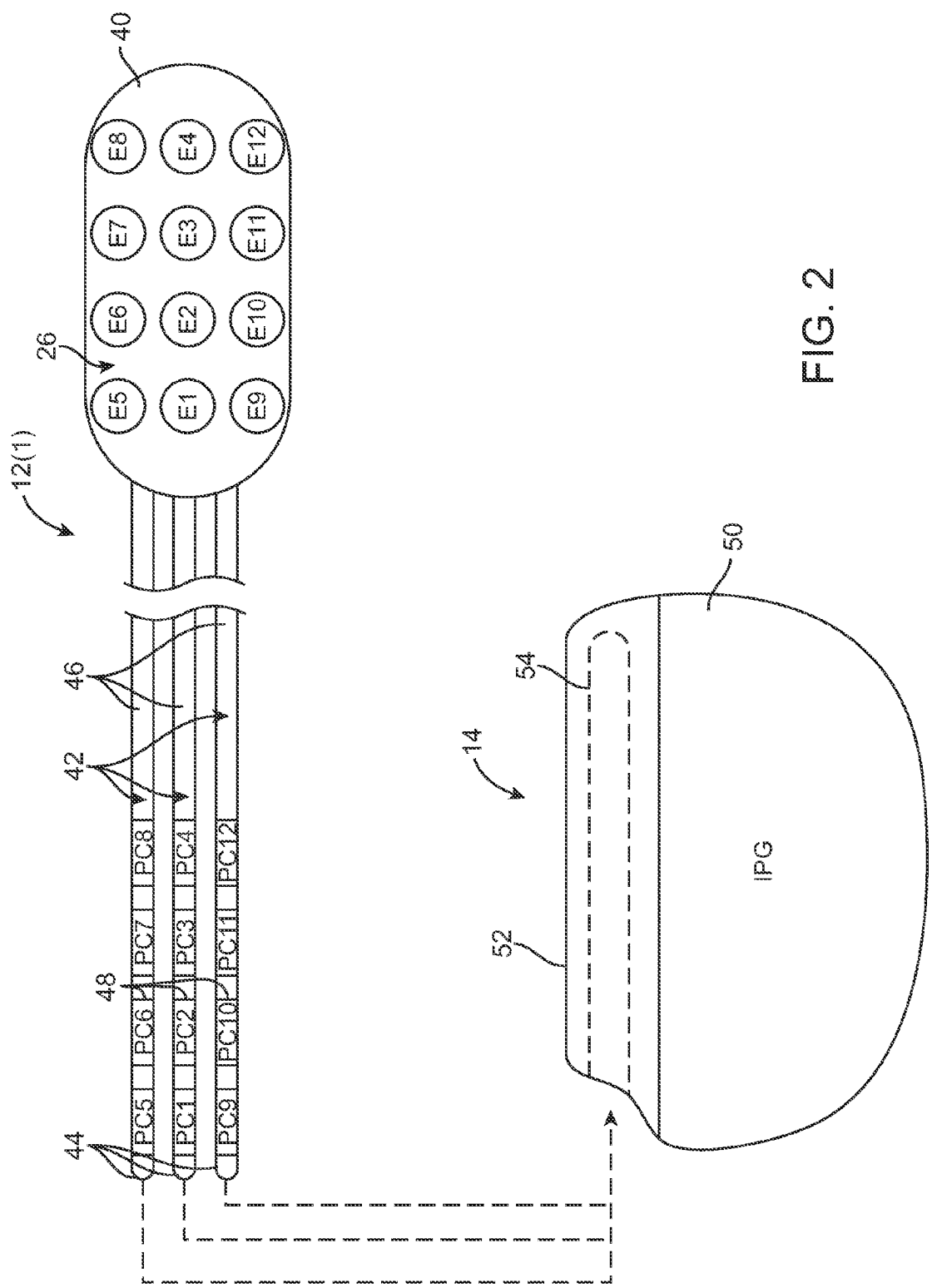
FIG. 2 is a plan view of an implantable pulse generator (IPG) and one embodiment of a surgical paddle stimulation lead used in the SCS system of FIG. 1.
Figure 3:
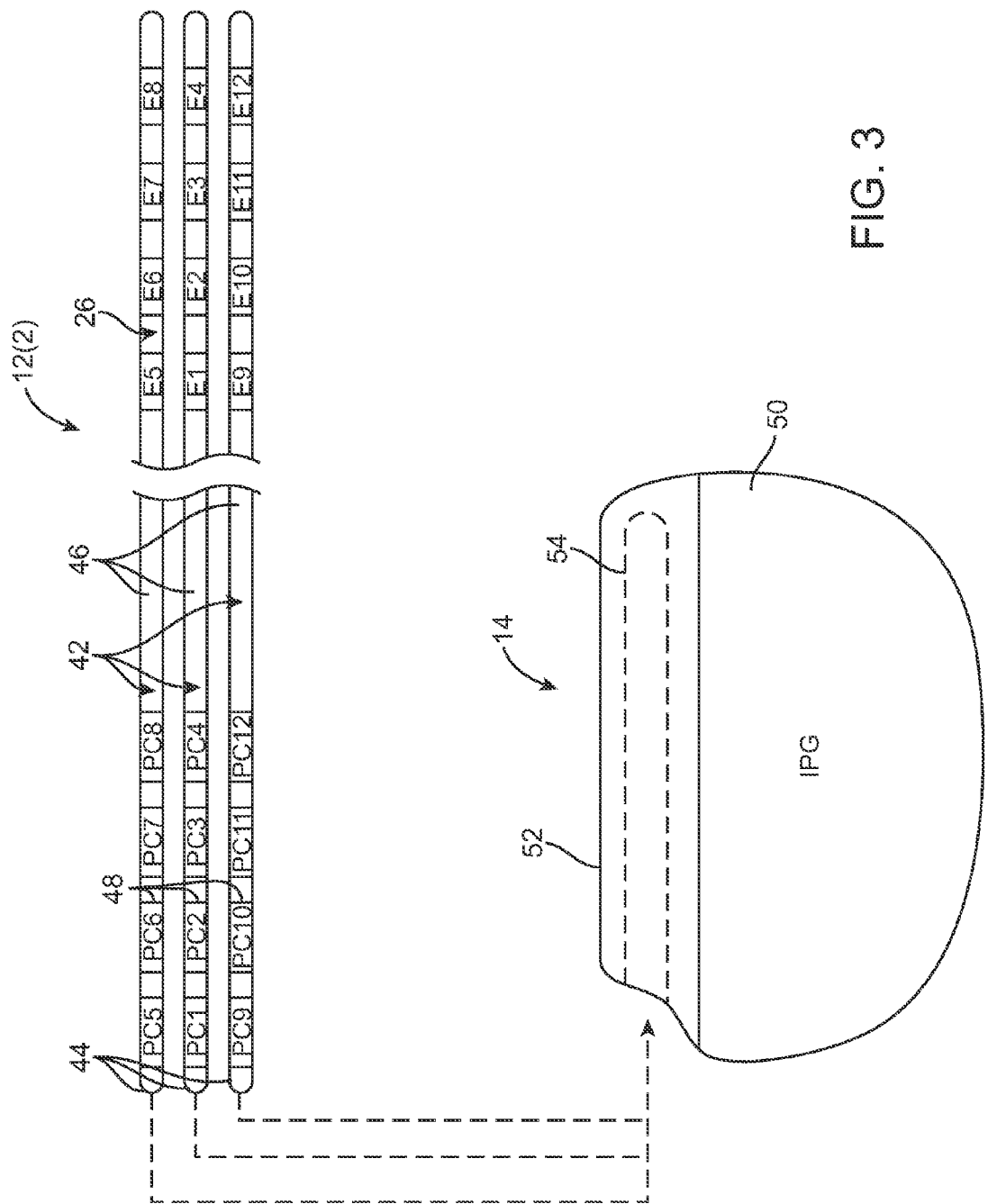
FIG. 3 is a plan view of an implantable pulse generator (IPG) and another embodiment of a percutaneous stimulation lead used in the SCS system of FIG. 1.

Referring to either of FIG. 2 or 3, the IPG 14 comprises an outer case 50 housing the electronic and other components (described in further detail below). The outer case 50 is composed of an electrically conductive, biocompatible material, such as titanium, and forms a hermetically sealed compartment wherein the internal electronics are protected from the body tissue and fluids. In some cases, the outer case 50 serves as an electrode. The IPG 14 further comprises a connector 52 in which the proximal ends 44 of the lead bodies 42 of the stimulation leads 12 can mate in a manner that electrically couples the electrodes 26 to the electronics contained within the outer case 50. To this end, the connector 52 includes a three ports 54 (only one shown in phantom) for receiving the proximal ends 44 of the three lead bodies 42 of the surgical paddle lead 12(1) or the proximal ends 44 of the three lead bodies 42 of the respective percutaneous leads 12(2). In the case where the lead extensions 24 are used, the ports 54 may instead receive the proximal ends of such lead extensions 24.

It should be noted that, although the lead bodies of the surgical paddle lead or the percutaneous leads will be described hereinafter as being mated with the ports, lead extensions can be considered to be lead bodies when mated with the respective surgical paddle lead or percutaneous leads. Thus, for the purposes of this specification, a "lead body" is simply an elongated member with proximal contacts that can be mated to a port of a neurostimulator to allow the electrodes on the surgical paddle lead or percutaneous lead to be electrically coupled to the circuitry contained within the neurostimulator. Furthermore, in some cases, a single extension lead can be specifically adapted to couple the three lead bodies 42 of the surgical lead 12(1) or percutaneous leads 12(2) to a single port. The significance for the present inventions is that three lead bodies, whether they be coupled to multiple ports or a single port, be identified relative to the columns of electrodes carried by the lead(s) 12.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 50, so that the electrical current has a path from the energy source contained within the IPG case 50 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 50 of the IPG 14, so that electrical energy is transmitted between the selected electrode 26 and case 50. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 4:
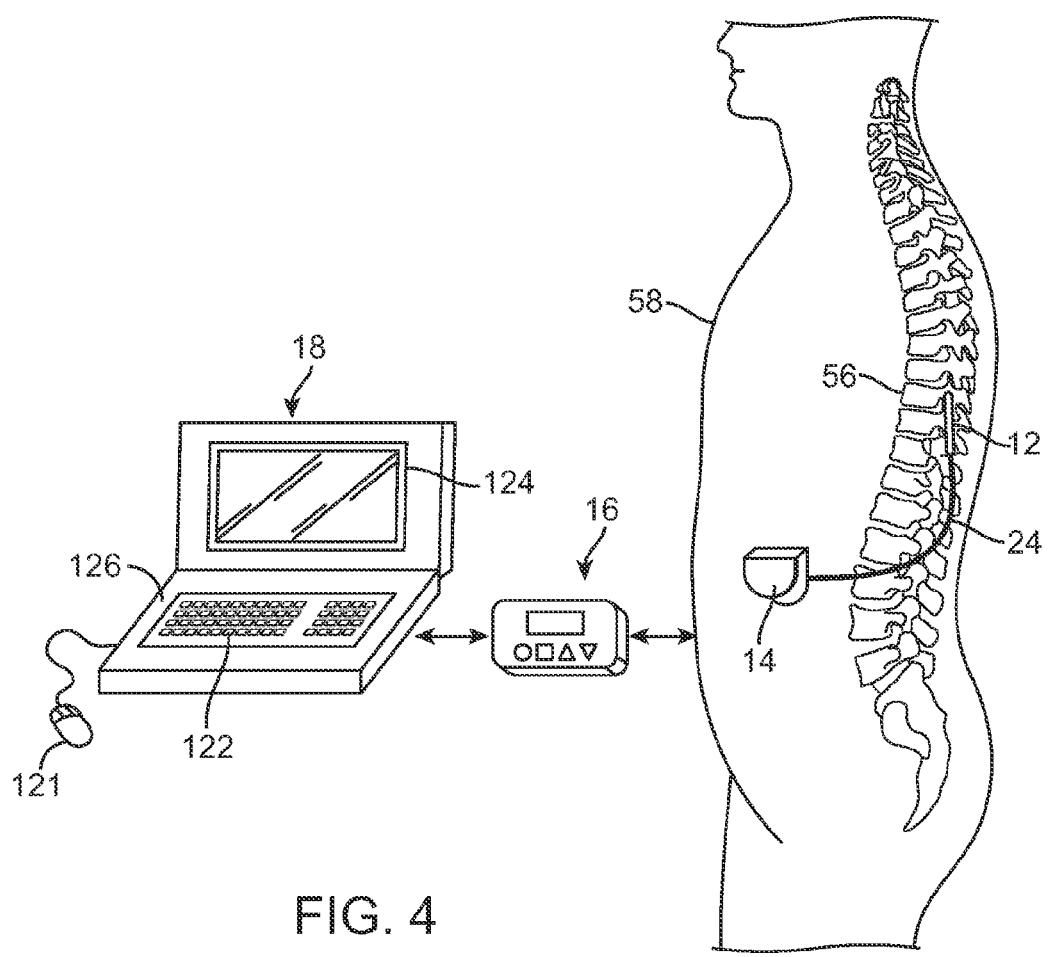
FIG. 4 is a plan view of the SCS system of FIG. 1 in use with a patient.

Referring to FIG. 4, the stimulation lead 12 (either 12(1) or 12(2)) is implanted within the spinal column 56 of a patient 58. The preferred placement of the electrode leads 12 is adjacent, i.e., resting near, or upon the dura, adjacent to the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16. While the electrode leads 12 are illustrated as being implanted near the spinal cord area of a patient, the electrodes leads 12 may be implanted anywhere in the patient's body, including a peripheral region, such as a limb, or the brain.

It can be appreciated from the foregoing that whether the surgical paddle lead 12(1) or three percutaneous leads 12(2) are used, three columns of electrodes 26 (in this case, E1-E4, E5-E8, and E9-E12) can be located along the spinal cord tissue. In this manner, three adjacent electrodes 26 from the respective electrode columns can be transversely placed across spinal cord tissue to form a medio-lateral electrode arrangement, with one of the electrodes 26 being used as a middle electrode, and the remaining two electrodes 26 being used as flanking electrodes. After implantation, the IPG 14 is used to provide the therapeutic stimulation under control of the patient.

Figure 5:
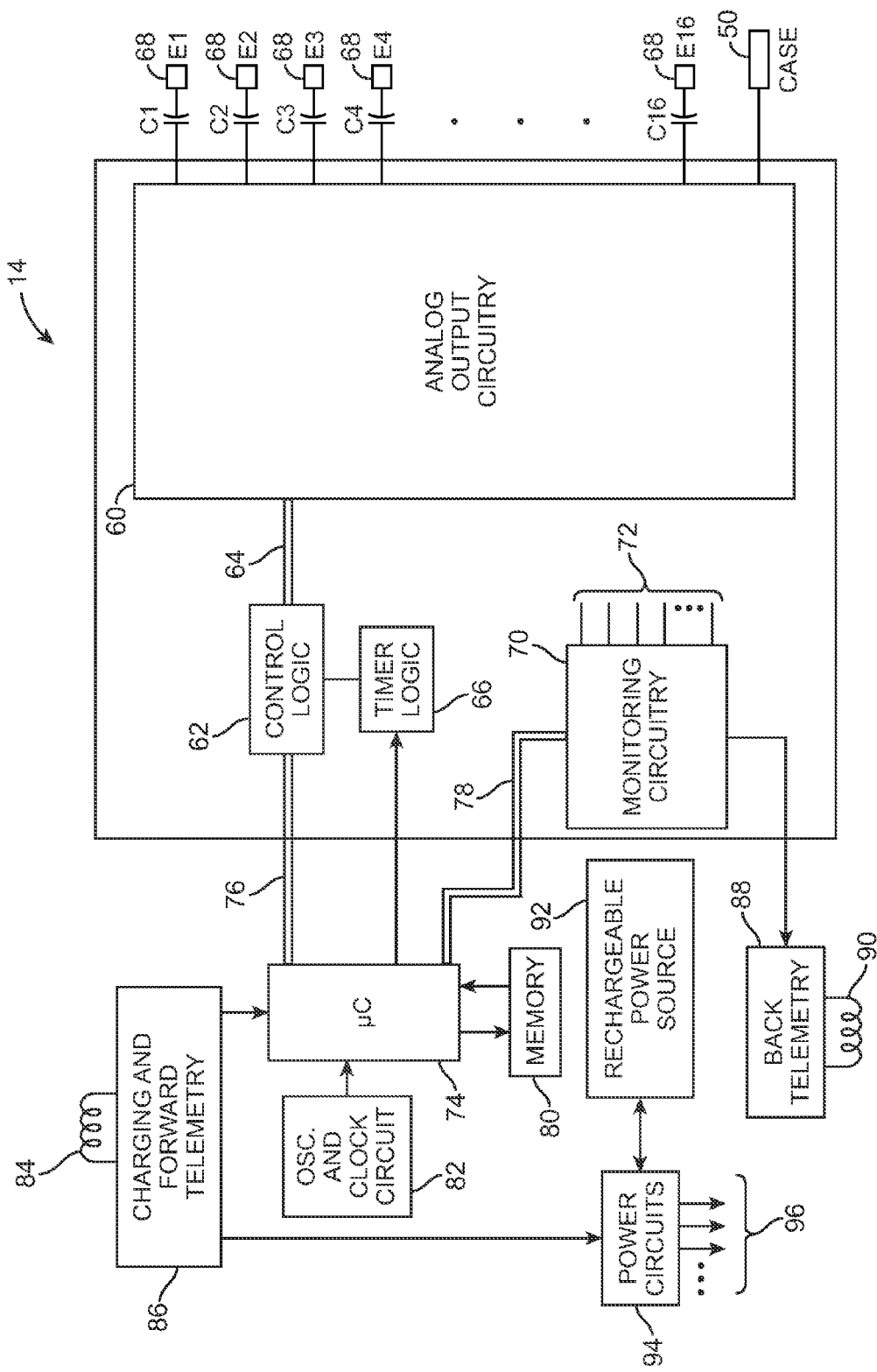
FIG. 5 is a block diagram of the internal components of the IPG of FIG. 1.

Turning next to FIG. 5, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 µs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. Significantly, the monitoring circuitry 70 is configured for taking such electrical measurements, so that, as will be described in further detail below, the CP 18 can automatically match the specific lead bodies 42 that are connected to the IPG 14 with the electrode columns carried by the lead or leads. In the illustrated embodiment, the electrical measurements taken by the monitoring circuitry 70 for the purpose of identifying the connected lead bodies, are field potentials or other electrical parameters (e.g., current and/or impedance) that may be used to derive the field potential. For the purposes of this specification, a field potential can either be directly measured or can be indirectly measured by directly measuring one or more different electrical parameter and then deriving the field potential from these electrical parameters. The monitoring circuitry 70 may also measure impedance at each electrode 26 in order to determine the coupling efficiency between the respective electrode 26 and the tissue and/or to facilitate fault detection with respect to the connection between the electrodes 26 and the analog output circuitry 60 of the IPG 14.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the field potential and impedance data) sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the AC receiving coil 84. To recharge the power source 92, an external charger (not shown), which generates the AC magnetic field, is placed against, or otherwise adjacent to, the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 5 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 6:
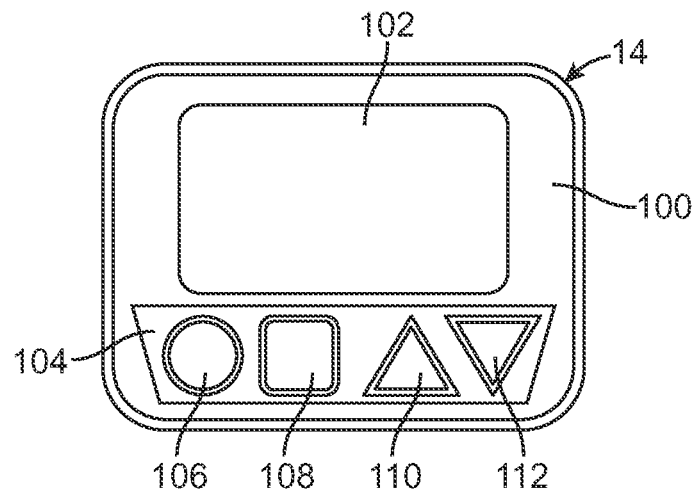
FIG. 6 is a plan view of a remote control (RC) that can be used in the SCS system of FIG. 1.

Referring now to FIG. 6, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can actuated to increment or decrement any of stimulation parameters of the pulse generated by the IPG 14, including pulse amplitude, pulse width, and pulse rate.

Figure 7:
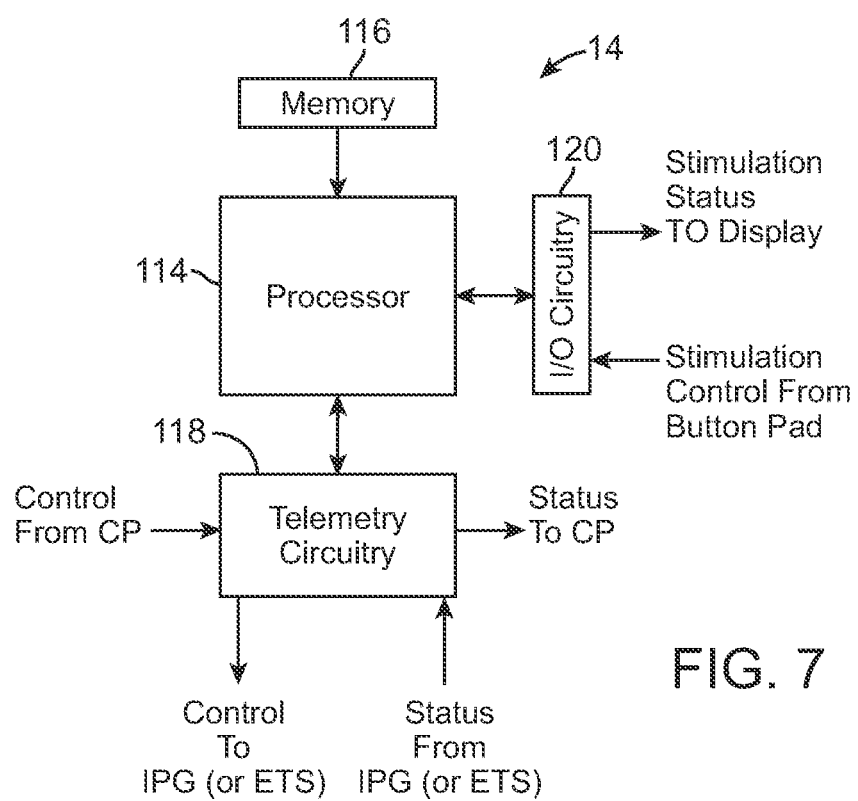
FIG. 7 is a block diagram of the internal componentry of the RC of FIG. 6.

Referring to FIG. 7, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 (or ETS 20) and receiving status information (including the measured electrical data) from the IPG 14 (or ETS 20) via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 6). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 4, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 8:
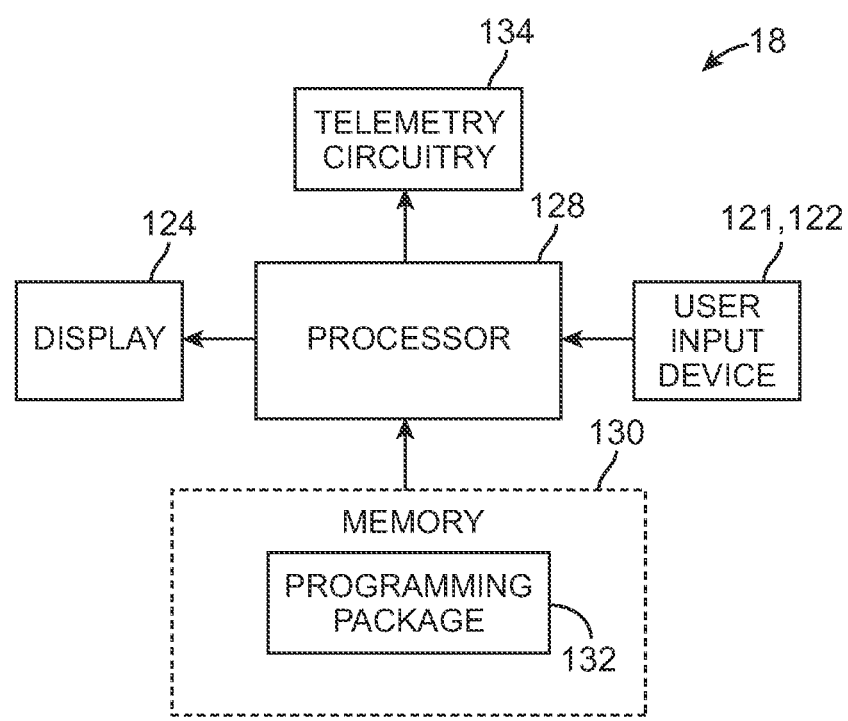
FIG. 8 is a block diagram of the components of a clinician's programmer that can be used in the SCS system of FIG. 1.

To allow the clinician to perform these functions, the CP 18 includes a mouse 121, a keyboard 122, and a programming display screen 124 housed in a case 126. It is to be understood that in addition to, or in lieu of, the mouse 121, other directional programming devices may be used, such as a joystick, or directional keys included as part of the keys associated with the keyboard 122. As shown in FIG. 8, the CP 18 generally includes a processor 128 (e.g., a central processor unit (CPU)) and memory 130 that stores a stimulation programming package 132, which can be executed by the processor 128 to allow a clinician to program the IPG 14 (or ETS 20) and RC 16. The CP 18 further includes telemetry circuitry 134 for downloading stimulation parameters to the RC 16 and uploading stimulation parameters already stored in the memory 116 of the RC 16 via link 36 (shown in FIG. 1). The telemetry circuitry 134 is also configured for transmitting the control data (including stimulation parameters and requests to provide status information) to the IPG 14 (or ETS 20) and receiving status information (including the measured electrical data) from the IPG 14 (or ETS 20) indirectly via the RC 16.

The CP 18 is configured for automatically identifying the lead body 42 (either the lead bodies of the surgical paddle lead 12(1) or the lead bodies of the percutaneous leads 12(2)) associated with the middle electrode column of the three electrode columns implanted within the patient based on a series of arranged (i.e., ordered) cross-electrode bipolar field potential measurements—one for each of the three electrode columns. Once the lead body 42 associated with the middle electrode column is identified, the CP 18 is configured for remapping the outputs (i.e., the ports) of the analog output circuitry 60 (shown in FIG. 5) to the proper electrodes 26 of the stimulation lead or leads 12 by transmitting appropriate control data to the IPG 14. Once the lead body 42 is identified and the outputs of the analog output circuitry 60 are mapped to the electrodes 26, the CP 18 can then generate stimulation parameters for use by the IPG 14 based on the identified lead body 42. Thus, the user may insert the lead body 42 into any port 54 of the connector 52 of the IPG 14 without concern that the incorrect connector port is being used.

For each field potential measurement, two electrodes (each located in one electrode column) are used to configure a bipolar arrangement of an anode and a cathode that generates an electrical field, and another electrode (located on the unused electrode column) is used to measure the potential of the electrical field. The three electrodes used to generate and measure the bipolar electrical field will be referred to herein as an electrode triplet.

Figure 9:
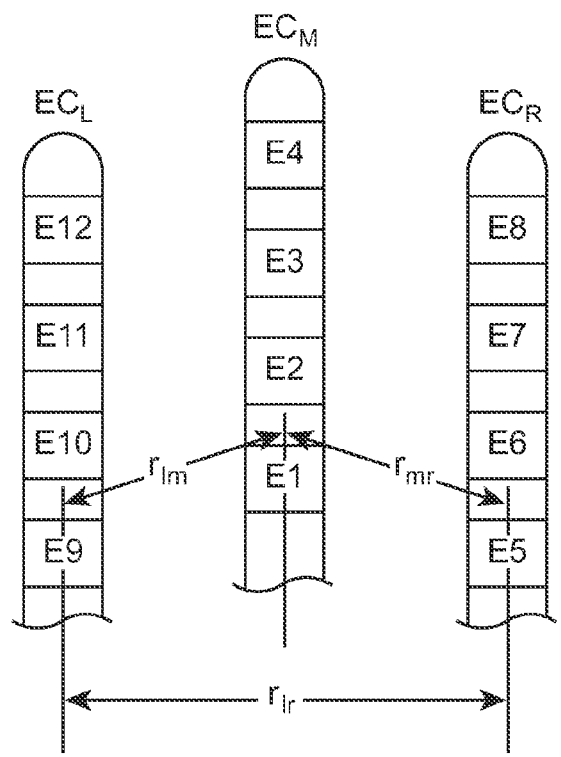
FIG. 9 is a plan view of one arrangement of electrode implanted within a patient.

An exemplary electrode column arrangement is illustrated in FIG. 9. As there shown, the middle electrode column is designated $EC_M$, the left electrode column is designated $EC_L$, and the right electrode column is designated $EC_R$. In this exemplary case, the respective electrode columns are longitudinally staggered. Notably, the electrode columns disposed on a surgical paddle lead 12(1) are generally designed to have no longitudinal stagger. However, some surgical paddle leads may be designed to have electrode columns that are longitudinally staggered. Of course, if percutaneous leads 12(2) are implanted in the patient, the electrode columns may have any varying degree of longitudinal stagger, depending on the manner in which the percutaneous leads 12(2) have been implanted within the patient or the migration of the percutaneous leads 12(2) from the original implantation site.

The three electrodes from the respective electrode columns that are selected as the triplet to be used for generating and measuring the electrical fields preferably have the least amount of longitudinal stagger in order to minimize any error in identifying the lead body associated with the middle electrode column $EC_M$. To determine the electrode triplet that has the least amount of longitudinal stagger, it will be necessary to determine the longitudinal stagger of the respective electrode columns. In the case where a surgical lead is used, the stagger of electrode columns, to the extent that there is a stagger, will be fixed, and thus known prior to its implantation within the patient. In the case where a surgical lead 12(1) with non-staggered electrode columns is used, any single row of three electrodes can be used as the electrode triplet. In the case where three percutaneous leads 12(2) are implanted within the patient, the extent that the leads 12(2), and thus the electrode columns, are longitudinally staggered will have to be determined after implantation. In this case, the longitudinal lead stagger may be determined using conventional means, such as fluoroscopy, or may be performed electronically using techniques described in U.S. patent application Ser. No. 11/557,484, entitled "System and Method for Computationally Determining Migration of Neurostimulation Leads," or U.S. Pat. No. 6,993,384, entitled "Apparatus and Method for Determining the Relative Position and Orientation of Neurostimulation Leads," which are expressly incorporated herein by reference.

Once the longitudinal lead stagger is determined, the electrode triplet can be selected either manually (e.g., user input into the CP 18) or automatically by the CP 18. In the illustrated embodiment, electrodes E1, E5, and E9 are selected, although other sets of adjacent electrodes, such as E2, E6, and E10, or E3, E7, and E11, or E4, E8, and E12 can be selected. Alternatively, more than one electrode triplet can be used to increase the accuracy or confidence of the lead body identification. As there shown, left and middle electrodes E9, E1 are separated by a distance $r_{lm}$, right and middle electrodes E5, E1 are separated by a distance $r_{mr}$, and left and right electrodes E9, E5 are separated by a distance $r_{lr}$.

Once the electrode triplet is selected, the CP 18 operates the IPG 14 (i.e., by transmitting a request for status information to the IPG 14 via the RC 16) to generate and measure bipolar electrical field potentials at the electrode triplet. In particular, the IPG 14 is instructed to convey bipolar electrical energy (via the analog output circuitry 60) between three different pairs of the three proximal contacts 48 corresponding to the selected electrode triplet, thereby generating bipolar electrical fields in the tissue between three respective pairs of electrodes 26 in the electrode triplet. While the respective electrical fields are being generated, the IPG 14 is also instructed to measure the potentials (via the monitoring circuitry 70) at the remaining electrodes 26 of the electrode triplets via the respective proximal contacts 48.

Figure 10:
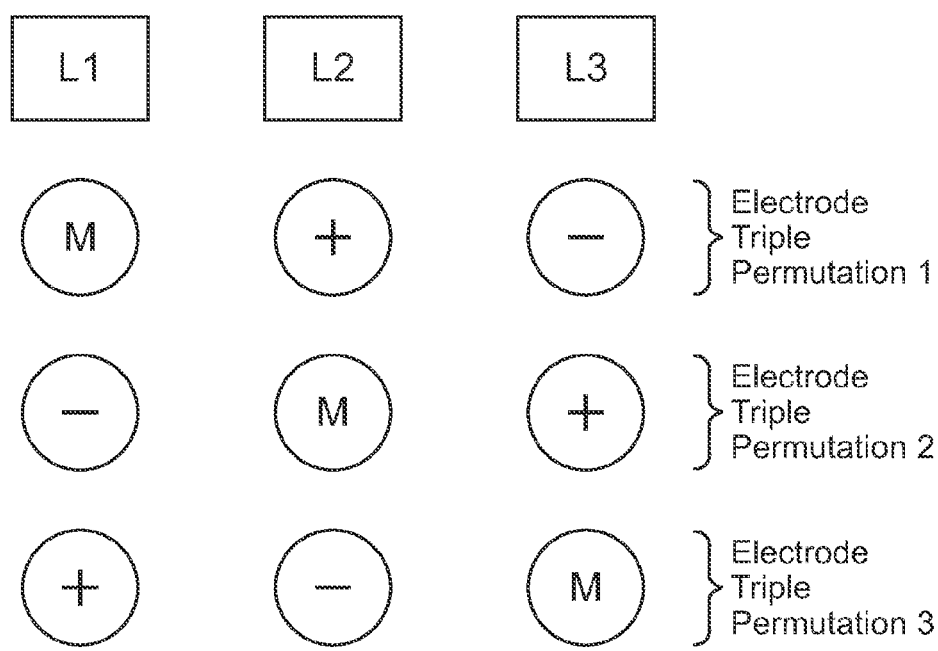
FIG. 10 is a representation illustrating various electrode triplets of the electrode arrangement of FIG. 9 that can be used by the SCS system of FIG. 1 to generate and measure bipolar electrical fields.

For example, with reference to FIG. 10, an electrode triplet is shown respectively coupled to arbitrarily assigned ports 54 of the IPG 14 (shown in FIGS. 2 and 3) via the proximal contacts 48 located on the lead bodies (either the lead bodies 42 of the surgical paddle lead 12(1) or the lead bodies 42 of the percutaneous leads 12(2). The lead bodies have been labeled L1, L2, and L3. The IPG 14 may source an electrical field (designated by "+") by passing an electrical current through a proximal contact 48 and the corresponding electrode 26, return the electrical field (designated by "−") by sinking the electrical current through a different proximal contact 48 and the corresponding electrode 26, and measure electrical field (designated by "M") by measuring a voltage potential at another different proximal contact 48 and the corresponding electrode 26 using different permutations of the selected electrode triplet. Three of these permutations are illustrated in FIG. 10.

In a first electrode triplet permutation, an electrical field is sourced at the electrode coupled to lead body L2, the electrical field is returned to the electrode coupled to lead body L3, and the potential of the electrical field is measured at lead body L1. In a second electrode triplet permutation, an electrical field is sourced at the electrode coupled to lead body L3, the electrical field is returned to the electrode coupled to lead body L1, and the potential of the electrical field is measured at lead body L2. In a third electrode triplet permutation, an electrical field is sourced at the electrode coupled to lead body L1, the electrical field is returned to the electrode coupled to lead body L2, and the potential of the electrical field is measured at lead body L3.

Other electrode permutations are also possible. For example, an electrical field can be sourced at the electrode coupled to lead body L2, the electrical field can be returned to the electrode coupled to lead body L1, and the potential of the electrical field can be measured at lead body L3. Or, an electrical field can be sourced at the electrode coupled to lead body L3, the electrical field can be returned to the electrode coupled to lead body L2, and the potential of the electrical field can be measured at lead body L1. Or, an electrical field can be sourced at the electrode coupled to lead body L1, the electrical field can be returned to the electrode coupled to lead body L3, and the potential of the electrical field can be measured at lead body L2.

The CP 18 records the amplitude value and polarity of the bipolar field potential measurement for each of the ports (i.e., lead bodies) in the order of measurement, compares the three values to each other to obtain a highest absolute value, and marks the port corresponding to the highest absolute value. Significantly, for the same sets of ports used to source and return the electrical fields, a single code or a set of codes (i.e., combination of amplitude values, polarity, and highest value of the bipolar field potential measurements) unique a specific port to which the middle electrode column is associated. Based on this unique code or codes, the CP 18 can determine the port (and thus the lead body) that is associated with the middle electrode column C. In some cases, the CP 18 will be able to determine, from these codes, whether or not the flanking electrode columns are equidistant from the middle electrode column, and if not equidistant, the port that is associated within the flanking electrode column closest to the middle electrode column, and the port that is associated with the flanking electrode column furthest from the middle electrode column.

A look-up table of unique reference codes (i.e., reference electrical field potential sets) and ordering of lead bodies can be stored, and the measured unique code can be compared to reference unique codes stored in a look-up table to obtain the corresponding lead body orders, and thus, the lead body corresponding to the middle electrode column C. The look-up table can be generated using empirically, or may be generated using heuristic principles, e.g., a field potential measurement taken at an electrode equi-distant between a source electrode and a return electrode will have a zero amplitude value, a field potential measurement taken at an electrode adjacent to a source electrode will have a positive polarization, a field potential measurement taken at an electrode adjacent to a return electrode will have a negative polarization, a field potential measurement taken at the flanking electrode that is closest to the middle electrode will have a maximum absolute value, etc.). For example, exemplary look-up tables are shown in FIGS. 11a-11c.

As provided in FIG. 11a, lead body L1 is determined to be associated with the middle electrode column $EC_M$ if: (a) the amplitude of the field potential measured at lead body L1 is approximately zero, and the polarizations of the field potentials measured at lead bodies L2 and L3 are respectively negative and positive (first and second rows); (b) the polarization of the field potentials measured at lead bodies L1-L3 are respectively negative, negative, and positive, and the field potential measured at lead body L3 has the highest absolute value (third and sixth rows); or (c) the polarization of the field potentials measured at lead bodies L1-L3 are respectively positive, negative, and positive, and the field potential measured at lead body L2 has the highest absolute value (fourth and fifth rows).

Figure 11B:

As provided in FIG. 11b, lead body L2 is determined to be associated with the middle electrode column $EC_M$ if: (a) the amplitude of the field potential measured at lead body L2 is approximately zero, and the polarizations of the field potentials measured at lead bodies L1 and L3 are respectively positive and negative (first and second rows); (b) the polarization of the field potentials measured at lead bodies L1-L3 are respectively positive, negative, negative, and the field potential measured at lead body L1 has the highest absolute value (third and sixth rows); and (c) the polarization of the field potentials measured at lead bodies L1-L3 are respectively positive, positive, and negative, and the field potential measured at lead body L3 has the highest absolute value (fourth and fifth rows).

Figure 11C:

As provided in FIG. 11c, lead body L3 is determined to be associated with the middle electrode column $EC_M$ if: (a) the amplitude of the field potential measured at lead body L3 is approximately zero, and the polarizations of the field potentials measured at lead bodies L1 and L2 are respectively negative and positive (first and second rows); (b) the polarization of the field potentials measured at lead bodies L1-L3 are respectively negative, negative, positive, and the field potential measured at lead body L2 has the highest absolute value (third and sixth rows); and (c) the polarization of the field potentials measured at lead bodies L1-L3 are respectively negative, positive, positive, and the field potential measured at lead body L1 has the highest absolute value (fourth and fifth rows).

The CP 18 can also use the look-up tables illustrated in FIGS. 11a-11c to determine whether or not the flanking electrode columns $EC_L$, $EC_R$ are equi-distant from the middle electrode column $EC_M$. In particular, the flanking electrode columns $EC_L$, $EC_R$ will be determined to be equi-distant to the middle electrode column (i.e., the electrode separation distances $r_{lm} \sim r_{mr} < r_{lr}$) if the bipolar field potential measurements yield the codes set forth in the first and second rows in any of the look-up tables illustrated in FIGS. 11a-11c.

The CP 18 can also use the look-up tables illustrated in FIGS. 11a-11c to determine, if the flanking electrode columns $EC_L$, $EC_R$ are not equi-distant from the middle electrode column $EC_M$ (i.e., the electrode separation distances $r_{lm} < r_{mr} < r_{lr}$ or $r_{mr} < r_{lm} < r_{lr}$), the lead body associated with the flanking electrode column closest to the middle electrode column $EC_M$ and the lead body associated with the flanking electrode column furthest from the middle electrode column $EC_M$.

Lead body L2 is determined to be associated with the flanking electrode column that is furthest from the middle electrode column $EC_M$, and lead body L3 is determined to be associated with the flanking electrode column that is closest to the middle electrode column $EC_M$ if the bipolar field potential measurements yield the codes set forth in third and sixth rows of the look-up table illustrated in FIG. 11a, while lead body L3 is determined to be associated with the flanking electrode column that is furthest from the middle electrode column $EC_M$, and lead body L2 is determined to be associated with the flanking electrode column that is closest to the middle electrode column $EC_M$ if the bipolar field potential measurements yield the codes set forth in fourth and fifth rows of the look-up table illustrated in FIG. 11a.

Lead body L3 is determined to be associated with the flanking electrode column that is furthest from the middle electrode column $EC_M$, and lead body L1 is determined to be associated with the flanking electrode column that is closest to the middle electrode column $EC_M$ if the bipolar field potential measurements yield the codes set forth in third and sixth rows of the look-up table illustrated in FIG. 11b, while lead body L1 is determined to be associated with the flanking electrode column that is furthest from the middle electrode column $EC_M$, and lead body L3 is determined to be associated with the flanking electrode column that is closest to the middle electrode column $EC_M$ if the bipolar field potential measurements yield the codes set forth in fourth and fifth rows of the look-up table illustrated in FIG. 11b.

Lead body L1 is determined to be associated with the flanking electrode column that is furthest from the middle electrode column $EC_M$, and lead body L2 is determined to be associated with the flanking electrode column $EC_M$ that is closest to the middle electrode column if the bipolar field potential measurements yield the codes set forth in third and sixth rows of the look-up table illustrated in FIG. 11c, while lead body L2 is determined to be associated with the flanking electrode column that is furthest from the middle electrode column $EC_M$, and lead body L1 is determined to be associated with the flanking electrode column that is closest to the middle electrode column $EC_M$ if the bipolar field potential measurements yield the codes set forth in fourth and fifth rows of the look-up table illustrated in FIG. 11c.

Although the CP 18 may not be able to match lead body to a specific flanking electrode column when the flanking electrode columns $EC_L$, $EC_R$ are equi-distant from the middle electrode column $EC_M$, it should be noted that, in this case, the user should be able to match the lead bodies to the respective flanking left and right electrode columns $EC_L$, $EC_R$ based on patient feedback. That is, if electrical stimulation is separately provided to the two lead bodies already known to be associated with the flanking electrode columns $EC_L$, $EC_R$ (by virtue of the fact that the lead body associated with the middle electrode column $EC_M$ has already been determined), based on the relative locations of the paresthesia felt by the patient when the electrical stimulation is provided to the two lead bodies, the user can associate each lead body with the proper flanking electrode column $EC_L$, $EC_R$.

It should be noted that due to the presence of noise in measurements, the lead body identified as having the highest absolute field potential value may differ from the lead body identified in the ideal case where there are no errors, and the field potential values identified as being approximately zero in the ideal case may be identified as being polarized if there are errors. However, the combination of the polarities during these error conditions are still unique for the different lead body-middle electrode column $EC_M$ associations, thereby allowing correct identification of the lead body associated with the middle electrode column $EC_M$ even in the presence of noise causes the measurements to deviate from the ideal case. For example, as set forth in the look-up tables in FIGS. 11a-11c, none of the polarity combinations of the bipolar field potential measurements that identify the lead body L1 as associated with the middle electrode column $EC_M$ are identical to any of the polarity combinations of the bipolar field potential measurements that identify the lead bodies L2 and L3 as being associated with the middle electrode column $EC_M$.

Figure 12:
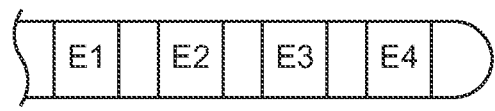
FIG. 12 is a partially cut-away plan view of a lead that can be used to generate reference electrical field potential sets.

Although the look-up tables illustrated in FIGS. 11a-11c have been briefly discussed as being generated empirically or heuristically prior to implantation of the leads within the patient, the look-up tables can be generated in real-time by using three electrodes coupled to a single lead body. For example, referring to FIG. 12, a first field potential measurement $FP_1$ can be taken at electrode E1 by sourcing a bipolar electrical field at electrode E2 and returning the electrical field at electrode E3; a second field potential measurement $FP_2$ can be taken at electrode E2 by sourcing a bipolar electrical field at electrode E3 and returning the electrical field at electrode E1; and a third field potential measurement $FP_3$ can be taken at electrode E3 by sourcing a bipolar electrical field at electrode E1 and returning the electrical field at electrode E2. Notably, other combinations of electrodes, such as electrodes E2, E3, and E4, or E1, E3 and E4 can be used, or electrodes from other electrode columns (e.g., electrodes E5, E6, E7) can be used, provided that the arrangement order of the selected electrodes is known.

Assuming that electrodes E1-E3 are respectively located within the left electrode column $E_L$, the middle electrode column $E_M$, and the right electrode column $E_R$, the field potential measurements $FP_1$-$FP_3$ can be permuted to obtain the reference electrical field potential sets (i.e., reference codes) for the association ordering between the lead bodies L1-L3 and electrode columns $E_L$, $E_M$, $E_R$. For example, for the case where the lead bodies L1-L3 are respectively associated with the left electrode column $E_L$, the middle electrode column $E_M$, and the right electrode column $E_R$, the reference electrical field potential set for this ordering will be [$FP_1$, $FP_2$, $FP_3$]. For the case where the lead bodies L1-L3 are respectively associated with the right electrode column $E_R$, the left electrode column $E_L$, and the middle electrode column $E_M$, the reference electrical field potential set for this ordering will be [$FP_3$, $FP_1$, $FP_2$]. For the case where the lead bodies L1-L3 are respectively associated with the middle electrode column $E_M$, the right electrode column $E_R$, and the left electrode column $E_L$, the reference electrical field potential set for this ordering will be [$FP_2$, $FP_3$, $FP_1$]. Similarly, one can also fix the reference field potential set of known arrangement order, and permute the measured field potential to match the reference.

Figure 13:
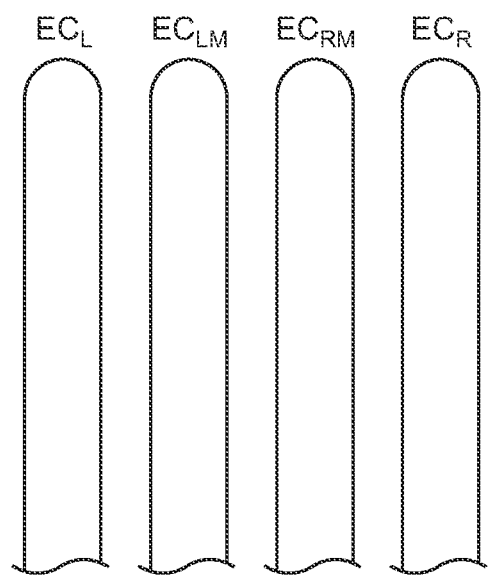
FIG. 13 is a representation illustrating four electrode columns and four associated lead bodies, wherein the SCS system of FIG. 1 can determine the lead body orientations relative to the electrode columns.
Figure 13:

It should be noted that the lead body auto-identification features described herein are not limited to three electrode columns arrangements, but can be applied to any three or more individual electrodes in a volume conductor. For example, with reference to FIG. 13, four lead bodies L1-L4 can be respectively matched with the four electrode columns (left electrode column $EC_L$, left-middle electrode column $EC_{LM}$, right-middle electrode column $EC_{RM}$, and right electrode column $EC_R$).

In particular, while ignoring lead body L4, lead bodies L1-L3 are operated to automatically determine which one is associated with a middle electrode column (either the left-middle electrode column $EC_{LM}$, right-middle electrode column $EC_{RM}$) in the same manner described above with respect to determining which of lead bodies L1-L3 is associated with the middle electrode column $EC_M$. The remaining two lead bodies can be matched to the flanking ones of the three electrode columns using patient feedback, as briefly discussed above. The ordering of the lead bodies L1-L3 with respect to the three associated electrode columns can be: [L1, L2, L3], [L3, L2, L1], [L2, L3, L1], [L1, L3, L2], [L3, L1, L2], or [L2, L1, L3].

Next, while ignoring the lead body associated with the middle electrode column, the lead bodies associated with the flanking electrode columns and lead body L4 are operated to automatically determine which one is associated with a middle electrode column (either the left-middle electrode column $EC_{LM}$, right-middle electrode column $EC_{RM}$) in the same manner described above with respect to determining which of lead bodies L1-L3 is associated with the middle electrode column $EC_M$. As one example, if the ordering of lead bodies L1-L3 in the first step was determined to be [L1, L2, L3], lead bodies L1, L3, and L4 will be operated to determine the lead body that is associated with the middle electrode column. Thus, the ordering of lead bodies L1, L3, and L4 with respect to the three associated electrode columns can be: [L1, L3, L4]; [L4, L1, L3], or [L1, L4, or L3].

If the ordering of the lead bodies is [L1, L3, L4], this determination combined with the determining of the ordering of the lead bodies in the first step of [L1, L2, L3] will yield an ordering of [L1, L2, L3, L4]. If the ordering of the lead bodies is [L4, L1, L3], this determination combined with the determining of the ordering of the lead bodies in the first step of [L1, L2, L3] will yield an ordering of [L4, L1, L2, L3]. If the ordering of the lead bodies is [L1, L4, L3], this determination combined with the determining of the ordering of the lead bodies in the first step of [L1, L2, L3] will yield an ordering of either [L1, L2, L4, L3] or [L1, L4, L2, L3].

In this latter case, the ordering of lead bodies L2 and L4 can be determined by operating either lead bodies L1, L2, L4 or lead bodies L2, L4, L3 to automatically determine which one is associated with a middle electrode column (either the left-middle electrode column $EC_{LM}$, right-middle electrode column $EC_{RM}$) in the same manner described above with respect to determining which of lead bodies L1-L3 is associated with the middle electrode column $EC_M$. If lead bodies L1, L2, L4 are operated, the ordering of the four lead bodies L1-L4 will be determined to be [L1, L2, L4, L3] if lead body L2 is determined to be associated with a middle electrode column, and [L1, L4, L2, L3] if lead body L4 is determined to be the middle electrode column. If lead bodies L2, L4, L3 are operated, the ordering of the four lead bodies L1-L4 will be determined to be [L1, L2, L4, L3] if lead body L4 is determined to be associated with a middle electrode column, and [L1, L4, L2, L3] if lead body L2 is determined to be the middle electrode column.

While the present inventions contemplate that the CP 18 may, itself, process or analyze the measured field potential information in order to effect identification of the lead bodies, the IPG 14 or the RC 16 may optionally have this capability. If the IPG 14, alone, performs the auto-identification function, it may remap its own ports without communication with the CP 18 or the RC 16. In this case, the RC 16 and/or CP 18 may conventionally operate with respect to the IPG 14. If the CP 18 requires the lead identification information, e.g., to display the relative displacement of the electrode columns, the CP 18 may appropriately request this information from the IPG 14 via a status request.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of operating three electrodes electrically coupled to three proximal contacts carried by three lead bodies, respectively, the electrodes adjacent tissue of a patient and including a middle electrode and a pair of electrodes flanking the middle electrode, the method comprising:
conveying electrical energy between at least one pair of the proximal contacts, thereby generating at least one electrical field in the tissue between at least one pair of the electrodes, respectively;
measuring a potential of the at least one electrical field at at least one remaining electrode via at least one remaining proximal contact, respectively; and
identifying the lead body associated with the middle electrode based on the at least one measured electrical field potential, wherein the at least one pair of the proximal contacts comprises three pairs of proximal contacts, the at least one pair of the electrodes comprises three pairs of electrodes, the at least one electrical field comprises three electrical fields, and the at least one measured electrical field potential comprise three measured electrical field potentials, and wherein the lead body associated with the middle electrode is identified at least partially based on a polarity of at least one of the three measured electrical field potentials.

2. A method of operating three electrodes electrically coupled to three proximal contacts carried by three lead bodies, respectively, the electrodes adjacent tissue of a patient and including a middle electrode and a pair of electrodes flanking the middle electrode, the method comprising:
conveying electrical energy between at least one pair of the proximal contacts, thereby generating at least one electrical field in the tissue between at least one pair of the electrodes, respectively;

measuring a potential of the at least one electrical field at at least one remaining electrode via at least one remaining proximal contact, respectively; and identifying the lead body associated with the middle electrode based on the at least one measured electrical field potential, wherein the three electrodes are respectively located within three electrode columns, the method further comprising determining a longitudinal stagger between the three electrode columns, and selecting the three electrodes from the respective electrode columns based on the determined longitudinal stagger.

3. The method of claim 2, wherein the electrodes selected from the respective electrode columns have the least amount of longitudinal stagger.

4. A method of operating three electrodes electrically coupled to three proximal contacts carried by three lead bodies, respectively, the electrodes adjacent tissue of a patient and including a middle electrode and a pair of electrodes flanking the middle electrode, the method comprising:

conveying electrical energy between at least one pair of the proximal contacts, thereby generating at least one electrical field in the tissue between at least one pair of the electrodes, respectively;

measuring a potential of the at least one electrical field at at least one remaining electrode via at least one remaining proximal contact, respectively; and identifying the lead body associated with the middle electrode based on the at least one measured electrical field potential, wherein the identification of the lead body comprises comparing the at least one measured electrical field potential to each of a plurality of reference electrical field potential sets respectively corresponding to different lead body orientations, determining a match between the at least one measured electrical field potential and one of the reference electrical field potential sets, and identifying the lead body associated with the middle electrode from the matching reference electrical field potential set.

5. A medical system, comprising:

one or more electrical leads comprising three electrodes and three lead bodies carrying three proximal contacts electrically coupled to the three electrodes, respectively, the electrodes configured for being placed adjacent tissue as a middle electrode and a pair of electrodes flanking the middle electrode;

a controller configured for transmitting electrical energy conveying electrical energy between at least one pair of the proximal contacts, thereby generating at least one electrical field in the tissue between at least one pair of the electrodes, respectively;

monitoring circuitry configured for measuring a potential of the at least one electrical field at at least one remaining electrode via at least one remaining proximal contact, respectively; and at least one processor configured for identifying the lead body associated with the middle electrode based on the at least one measured electrical field potential, wherein the at least one pair of the proximal contacts comprises three pairs of proximal contacts, the at least one pair of the electrodes comprises three pairs of electrodes, the at least one electrical field comprises three electrical fields, and the at least one measured electrical field potential comprise three measured electrical field potentials, and wherein the at least one processor is configured for identifying the lead body associated with the middle electrode at least partially based on a polarity of at least one of the three measured electrical field potentials.

6. A medical system, comprising:

one or more electrical leads comprising three electrodes and three lead bodies carrying three proximal contacts electrically coupled to the three electrodes, respectively, the electrodes configured for being placed adjacent tissue as a middle electrode and a pair of electrodes flanking the middle electrode;

a controller configured for transmitting electrical energy conveying electrical energy between at least one pair of the proximal contacts, thereby generating at least one electrical field in the tissue between at least one pair of the electrodes, respectively;

monitoring circuitry configured for measuring a potential of the at least one electrical field at at least one remaining electrode via at least one remaining proximal contact, respectively; and at least one processor configured for identifying the lead body associated with the middle electrode based on the at least one measured electrical field potential, wherein the three electrodes are respectively located within three electrode columns, the at least one processor further configured for determining a longitudinal stagger between the three electrode columns, and selecting the three electrodes from the respective electrode columns based on the determined longitudinal stagger.

7. The medical system of claim 6, wherein the at least one processor is configured for selecting the electrodes from the respective electrode columns that have the least amount of longitudinal stagger.

8. A medical system, comprising:

one or more electrical leads comprising three electrodes and three lead bodies carrying three proximal contacts electrically coupled to the three electrodes, respectively, the electrodes configured for being placed adjacent tissue as a middle electrode and a pair of electrodes flanking the middle electrode;

a controller configured for transmitting electrical energy conveying electrical energy between at least one pair of the proximal contacts, thereby generating at least one electrical field in the tissue between at least one pair of the electrodes, respectively;

monitoring circuitry configured for measuring a potential of the at least one electrical field at at least one remaining electrode via at least one remaining proximal contact, respectively;

at least one processor configured for identifying the lead body associated with the middle electrode based on the at least one measured electrical field potential; and memory storing a plurality of reference electrical field potential sets respectively corresponding to different lead body orientations, wherein the at least one processor is configured for identifying the lead body by comparing the at least one measured electrical field potential to each of the reference electrical field potential sets, determining a match between the at least one measured electrical field potential and one of the reference electrical field potential sets, and identifying the lead body associated with the middle electrode from the matching reference electrical field potential set.

* * * * *